United States Patent [19]

Kim

[11] Patent Number: 4,843,720

[45] Date of Patent: Jul. 4, 1989

[54] DENTAL MEASURING INSTRUMENT

[76] Inventor: Daniel S. Y. Kim, 7621 SE. Maple Ave., Vancouver, Wash. 98664

[21] Appl. No.: 202,397

[22] Filed: Jun. 6, 1988

[51] Int. Cl.$^4$ ............ G01B 5/02; G01B 3/38; A61C 19/04

[52] U.S. Cl. ................ 33/812; 33/512; 33/811; 33/513; 128/777; 433/72

[58] Field of Search .......... 33/513, 514, 143 C, 33/143 M, 143 J, 143 K, 147 T, 147 J, 485, 486; 128/777; 433/72; 235/70 A, 70 B; 40/353, 355, 356

[56] References Cited

U.S. PATENT DOCUMENTS

| | | | |
|---|---|---|---|
| 526,926 | 10/1884 | Littell | 33/143 J |
| 1,726,193 | 8/1929 | Ross | 33/513 |
| 1,901,724 | 3/1933 | Bennett | 33/513 |
| 2,154,148 | 4/1939 | Butts | 33/513 |
| 2,190,472 | 2/1940 | Ferrughelli | 235/70 R |
| 2,305,376 | 12/1942 | Blum | 33/143 M |
| 2,512,042 | 6/1950 | Stern | 33/143 J |
| 2,535,163 | 12/1950 | Scott | 33/513 |
| 3,797,118 | 3/1974 | Yamamoto | 33/158 |
| 4,718,850 | 1/1988 | Knebelman | 33/513 |

FOREIGN PATENT DOCUMENTS

| | | | |
|---|---|---|---|
| 61533 | 3/1892 | Fed. Rep. of Germany | 33/143 J |
| 663320 | 8/1938 | Fed. Rep. of Germany | 33/143 J |

Primary Examiner—William A. Cuchlinski, Jr.
Assistant Examiner—Patrick R. Scanlon
Attorney, Agent, or Firm—Lee R. Schermerhorn

[57] ABSTRACT

A dual purpose instrument having parts to measure the width of the nose and parts to measure the vertical distance from the underside of the chin to the underside of the nose, for use in making dentures.

6 Claims, 1 Drawing Sheet

DENTAL MEASURING INSTRUMENT

BACKGROUND OF THE INVENTION

This invention relates to an instrument particularly for measuring certain vertical and horizontal dimensions on the human face for use in making dentures, but the instrument is not limited to any particular use.

Two long-standing and troublesome problems in making dentures are obtaining the proper occlusion or bite between the upper or lower dentures and to determine the width of the teeth. The fit, appearance and the functional operation of dentures are extremely important, and have long been quite difficult to accomplish.

Most previous devices for this purpose have been of complicated and expensive construction and often difficult to use.

SUMMARY OF THE INVENTION

The present instrument has two primary functions: To measure the vertical distance from the underside of the chin to the underside of the nose, and to measure the width of the nose from ala to ala. A measuring strip has a transverse gauge block fixedly mounted on one end thereof. Slidably mounted on the measuring strip is a second transverse gauge block movable toward and away from the fixed block.

For measuring the width of the nose, the two gauge blocks have confronting nose engaging surfaces on one end of the gauge blocks at one side of the measuring strip.

For measuring the distance from the underside of the chin to the underside of the nose, the two gauge blocks have nonconfronting face engaging surfaces at the opposite side of the measuring strip. When the measuring strip is vertically positioned in front of the face, a horizontal top edge surface on the fixed block engages the underside of the nose, and a horizontal surface on the movable block engages the underside of the chin.

Thus the instrument has separate parts to measure both the horizontal and vertical facial dimensions necessary for making well fitting and comfortably functional dentures. The present form of construction is of relatively simple and inexpensive two dimensional design which is durable, easy to use and convenient to handle.

The invention will be better understood and additional features and advantages will become apparent from the following description of the preferred embodiment illustrated in the accompanying drawing. Various changes may be made in the details of construction and arrangement of parts and certain features may be used without others. All such modifications within the scope of the appended claims are included in the invention.

DESCRIPTION OF THE PREFERRED EMBODIMENT

Fixedly mounted on one end of a flat measuring strip 10 is a gauge block 12 projecting on opposite sides of the measuring strip. An elongated transverse measuring block 14 is slidably mounted on measuring strip 10 with the ends of the block projecting from opposite sides of the measuring strip in the plane of the fixed block 12.

Figure 4:
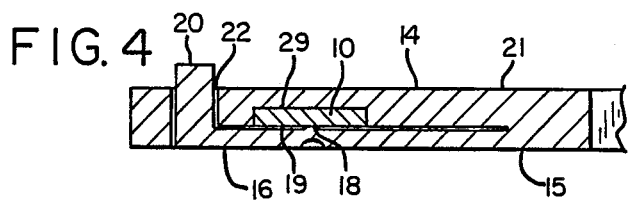
FIG. 4 is a sectional view on the line 4—4 in FIG. 2.
Figure 5:
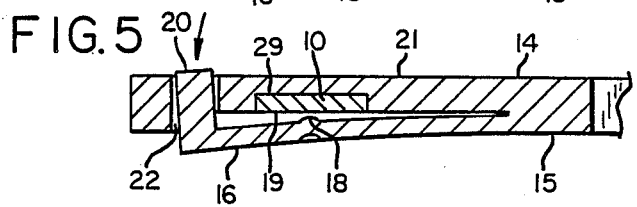
FIG. 5 is a view corresponding to FIG. 4 with the slide clamping tongue released from the measuring strip.

As seen in FIGS. 4 and 5 the back face 15 of block 14 has a resilient tongue 16 with a lug 18 normally pressing against a smooth back face surface 19 of the measuring strip 10 to prevent free sliding of block 14 on the measuring strip. The free end of tongue 16 has a push button projection 20 which projects forward through an opening 22 in the front face 21 of block 14, whereby depressing the push button 20 disengages lug 18 from the measuring strip to allow free sliding movement of block 14 on the measuring strip.

Figure 6:
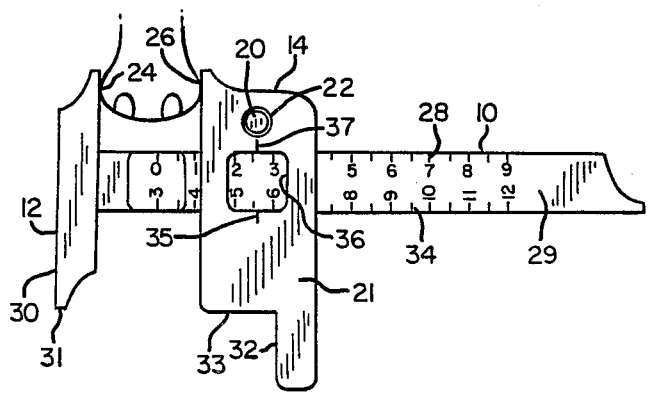
FIG. 6 is a view showing how the instrument is applied to measure the width of the nose.

As seen in FIG. 6 the fixed block 12 has a flat surface 24 on one end of the block to engage one side of the nose and the sliding block 14 has a parallel flat confronting surface 26 to engage the opposite side of the nose for measuring the width of the nose. This dimension is read on a scale 28 along one side edge of the front face 29 of the measuring strip.

Figure 7:
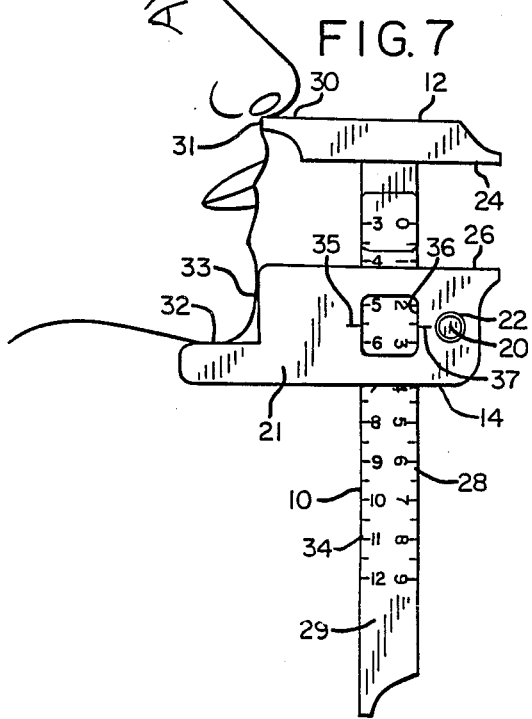
FIG. 7 is a view showing how the instrument is applied to measure the distance from the underside of the chin to the underside of the nose.

In FIG. 7 an upward facing flat surface 30 on the opposite end of fixed block 12 engages the underside of the nose and an upward facing flat surface 32 on the corresponding end of block 14 engages the underside of the chin to measure the vertical distance from the underside of the chin to the underside of the nose. This distance is read on a scale 34 on the front face 29 of measuring strip 10.

Figure 1:
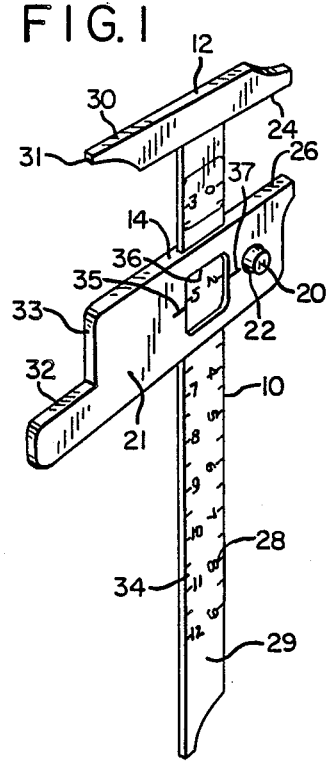
FIG. 1 is a perspective view of the front side of the instrument.
Figure 2:
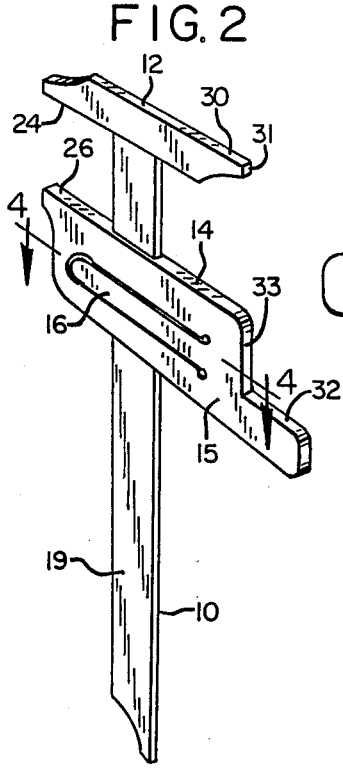
FIG. 2 is a perspective view of the back side of the instrument.
Figure 3:
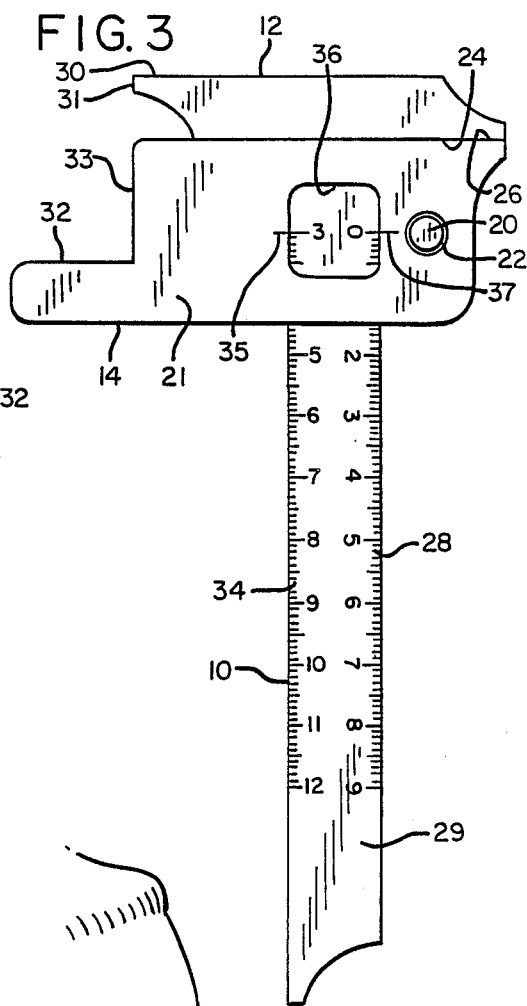
FIG. 3 is a vertical elevation view.

In FIGS. 3 and 7 the horizontal edge 32 on slide block 14 extends back to a vertical edge 33 aligned with the end 31 of fixed block 12.

Scale 28 is read at index line 37 and scale 34 is read at index line 35, on opposite sides of window opening 36 in the front face 21 of slide block 14.

Thus the right ends of gauge blocks 12 and 14 in FIGS. 3 and 7 are applied to the nose as shown in FIG. 6 to measure the width of the nose and the left ends of the gauge blocks in FIGS. 3 and 7 are applied to the chin and nose to measure the vertical distance therebetween as shown in FIG. 7, whereby both horizontal and vertical measurements are easily made with the one instrument.

What is claimed is:

1. A measuring instrument comprising a measuring strip having a transverse gauge block fixedly mounted on one end thereof, a transverse slide block mounted for sliding movement along said strip toward and away from said fixed block, a resilient tongue on one face of said slide block extending across said measuring strip and having one end connected to one end of said slide block beyond one side edge of said strip, a lug on said tongue arranged to engage and clamp against a continuous smooth surface on one face of said strip within said slide block, and a push button on the opposite end of said tongue movable in an opening in the opposite end of said slide block beyond the opposite side edge of said strip and accessible on the opposite face of said slide block to bend said tongue and disengage said lug from said strip.

between said two nonconfronting object engaging surfaces on said blocks, and a window opening in said slide block for reading said two scales.

5. An instrument as defined in claim 4, said two scales being on the opposite face of said strip from the face said slide block extending horizontally from a free end of said slide block back to a vertical outward facing edge aligned with said free end of said fixed block.

\* \* \* \* \*